United States Patent [19]

Ohmori et al.

[11] Patent Number: 5,157,148

[45] Date of Patent: Oct. 20, 1992

[54] FLUORINE-CONTAINING ALICYCLIC AND AROMATIC CYCLIC COMPOUNDS, PROCESS THEREOF AND ADHESIVE COMPOSITION CONTAINING THE COMPOUND

[75] Inventors: Akira Ohmori, Ibaraki; Yoshiki Shimizu, Nabari; Motonobu Kubo, Toyonaka; Kouzaburou Nakamura, Tokyo; Tohru Maruno, Ibaraki; Norio Murata, Tokyo; Hideo Kobayashi, Settsu, all of Japan

[73] Assignees: Daikin Industries, Ltd., Osaka; Nippon Telegraph and Telephone Corporation, Tokyo, both of Japan

[21] Appl. No.: 587,131

[22] Filed: Oct. 18, 1990

Related U.S. Application Data

[62] Division of Ser. No. 205,853, Jun. 13, 1988, abandoned.

[30] Foreign Application Priority Data

Jun. 15, 1987 [JP] Japan .................. 62-149784
Dec. 8, 1987 [JP] Japan .................. 62-308556

[51] Int. Cl.$^5$ ...................... C07C 69/52; C07C 69/62
[52] U.S. Cl. ................................. 560/219; 560/220; 560/223
[58] Field of Search ............ 560/220, 223, 220, 219

[56] References Cited

U.S. PATENT DOCUMENTS

| | | | |
|---|---|---|---|
| 4,360,693 | 11/1982 | Orlowski | 560/220 |
| 4,556,729 | 12/1985 | Kubo et al. | 560/220 |
| 4,767,883 | 8/1988 | Molaire | 560/220 |

*Primary Examiner*—Paul J. Killos
*Attorney, Agent, or Firm*—Nikaido, Marmelstein, Murray & Oram

[57] ABSTRACT

Fluorine-containing alicyclic or aromatic cyclic compounds represented by the formula

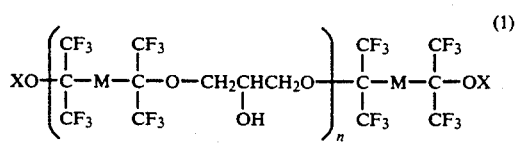

wherein M is a divalent organic group comprising at least one substituted or unsubstituted alicyclic hydrocarbon group or a divalent organic group comprising at least two substituted or unsubstituted aromatic hydrocarbon group, the alicyclic hydrocarbon group or aromatic hydrocarbon group may be linked by O, S or $CH_2$, or may form a condensed ring, X is

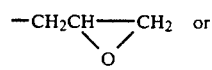

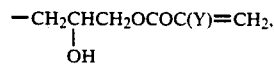

Y is H or $CH_3$, n is zero or a positive number, are useful as an effective component of the adhesive composition.

1 Claim, 3 Drawing Sheets

FLUORINE-CONTAINING ALICYCLIC AND AROMATIC CYCLIC COMPOUNDS, PROCESS THEREOF AND ADHESIVE COMPOSITION CONTAINING THE COMPOUND

This is a division of application Ser. No. 205,853 filed Jun. 13, 1988, now abandoned.

The present invention relates to a fluorine-containing alicyclic and aromatic cyclic compound, a process for preparing the same and adhesive composition containing the compound.

With a development in optical communication, requirements are increased for organic materials which are suitable to mold a lens or prism or to adhere an optical part with an another part. Particularly, it is required for an optical adhesive used to adhere an optical part (1) to be low in refractive index in order to match with a glass or like optical part in refractive index, and (2) to be cured at a low temperature in order not to afford a high temperature to the neighboring parts in the adhesion process.

Conventionally, epoxy resin compositions have been mainly used to the above use. Since usually available bisphenol A type epoxy resins are too high in refractive index (1.55 to 1.58), an adhesive composition which is low in refractive index and contains a bisphenol A type epoxy resin having introduced fluorine atom therein is disclosed, for example, in Japanese Patent Application No. 217794/1983.

However, these conventional compositions are still high in refractive index (1.51 to 1.58) and have a drawback that the reflection loss is large at the interface with quartz (refractive index 1.46), another optical part. Further, light returning by reflection from the interface has a defect to render unstable the operation of a laser diode light source.

An object of the invention is to provide a new fluorine-containing alicyclic or aromatic cyclic compound, which is excellent in heat-resistance and strength, as well as water-resistance and refractive index, a process for preparing the same; and adhesive composition containing the compound.

The above and other objects of the invention will become apparent from the following description.

The present invention provides fluorine-containing alicyclic and aromatic cyclic compounds represented by the formula

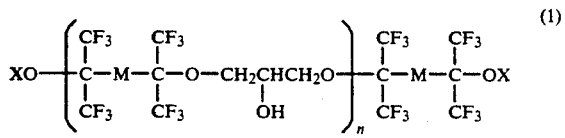

wherein M is a divalent organic group comprising at least one substituted or unsubstituted alicyclic hydrocarbon group or a divalent organic group comprising at least two substituted or unsubstituted aromatic hydrocarbon group, the alicyclic hydrocarbon group or aromatic hydrocarbon group may be linked by O, S or CH$_2$, or may form a condensed ring, X is

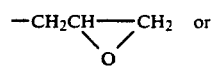

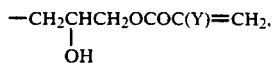

Y is H or CH$_3$, n is zero or a positive number, and a process for preparing the same and adhesive composition containing the compound.

In the formula (1) of the present invention, preferred examples of divalent organic groups comprising alicyclic hydrocarbon group and represented by M are

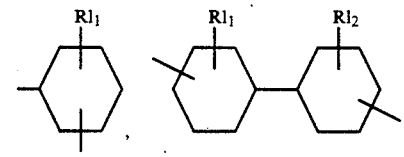

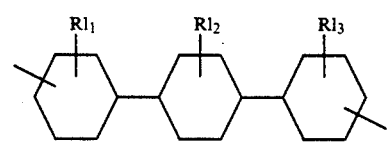

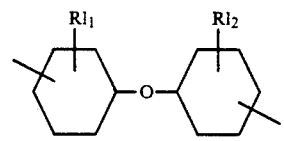

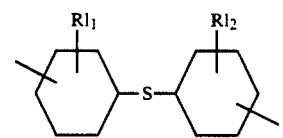

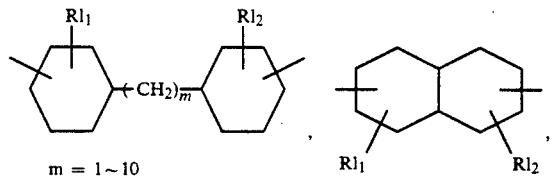

m = 1~10

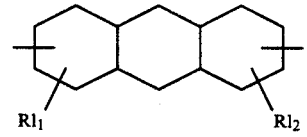

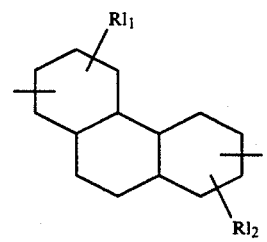

wherein R is a substituent, $l_1$, $l_2$ and $l_3$ are each zero or an integer of 1 or 10 and represent a number of the substituent R's, R's being same or different when the number is two or more, and also even in the case the number is one, R's being same or different when R are present in at least two in an organic group. Examples of the substituent R are alkyl group having 1 to 5 carbon atoms, OH, CH$_3$, NH$_2$, halogen atom (F, Cl, Br, etc.) and fluoroalkyl group having 1 to 20 carbon atoms.

Typical examples of divalent organic groups comprising aromatic hydrocarbon group and represented by M are all of those enumerated in the above examples of alicyclic hydrocarbon groups in which the cyclohexane ring is changed to the benzene ring and the first example is excluded. Specific examples thereof are as follows.

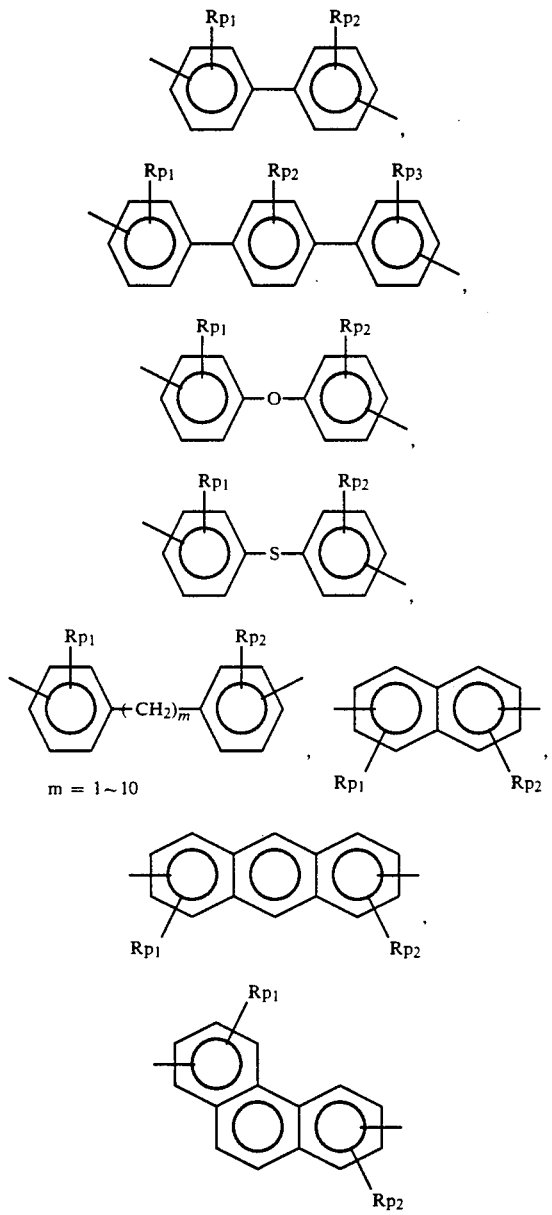

wherein R is a substituent, p$_1$, p$_2$ and p$_3$ are each zero or an integer of 1 to 4 and represent a number of the substituent R, R's being same or different when the number is two or more, and also even in the case the number is one, R's being same or different when γR's are present in at least two in an organic group. Examples of the substituent R are alkyl group having 1 to 5 carbon atoms, OH, CH$_3$, NH$_2$, halogen atom (F, Cl, Br, etc.) and fluoroalkyl group having 1 to 20 carbon atoms.

X is glycidyl group (Gly group) or a group obtained by reacting acrylic acid and or methacrylic acid with Gly group, n is zero or a positive number and is preferably 0 to 30.

The above fluorine-containing compound of the present invention can be prepared, for example, by (a) reacting a compound of the formula

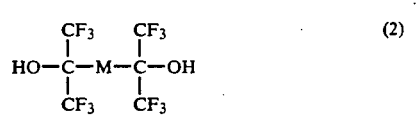

when epichlorohydrin (ECH) and dehydrochloride agent, or (b) further reacting acrylic acid or methacrylic acid with the product of the above (a), wherein M is same as above.

While solvent is not necessarily required in the reaction (a), methyl ethyl ketone (MEK), methyl isobutyl ketone (MIBK) and the like can be used as a solvent. ECH is used preferably in an amount of about 2 to 100 moles per mole of the compound (2). Further, NaOH, KOH, LiOH, Ca(OH)$_2$ or like dehydrochloride agent is used, preferably in an amount of about 1 to 20 equivalents per equivalent of OH of the compound (2). While catalyst is not necessarily required, trimethylbenzylammonium chloride, tetramethylammonium bromide, or like quaternary ammonium salt, can be used as a catalyst in an amount of about 0.01 to 10% by weight in the reaction system. The reaction temperature can be suitably selected and is preferably a temperature in the range of about 50° to 200° C.

In the reaction (b) of the diglycidyl ether as obtained in the above reaction (a) with acrylic acid or methacrylic acid, while solvent is not necessarily required, benzene, toluene, xylene, MEK, MIBK or the like can be employed as a solvent. It is preferable to use an acid in an amount of about 1 to 50 moles per equivalent of epoxy group of the diglycidyl ether. As a catalyst, when required, trimethylbenzylammonium chloride, tetramethylammonium bromide or like quaternary ammonium salt or trimethylamine, triethylamine or like tertiary amine is used in an amount of about 0.1 to 10% by weight in the reaction system. As a thermal polymerization inhibitor, when required, hydroquinone, hydroquinone monoethyl ether, catechol, t-butylcatechol, phenotiazine or the like is used preferably in an amount of about 0.001 to 10% by weight in the reaction system. The reaction temperature can be suitably selected and is preferably a temperature in the range of about 50° to 200° C.

The desired fluorine-containing compound of the formula (1) can be isolated or purified by a usual method such as extraction, concentration, distillation and recrystallization.

Among the fluorine-containing compounds of the present invention, the epoxy compound wherein X is Gly group can be used as an adhesive with a conjoint use of (a) a curing agent for epoxy resins such as a polyamine, polyol and acid anhydride.

(b) a thermal curing catalyst for epoxy resins such as imidazoles and Lewis acids (BF$_3$ complex, etc.), or (c) a photo-curing catalyst for epoxy resins such as a diazonium salt, a sulfonium salt and phosphonium salt.

Among the fluorine-containing compounds of the present invention, the compound having acryloxy groups or methacryloyloxys group can be used as an adhesive with addition of a known thermal polymerization initiator such as an azo compound (azobisisobutyronitrile, etc.) and a peroxide (benzoyl peroxide, etc.). Further, the compound can be employed as an adhesive by a conjoint use with a photopolymerization initiator (benzophenone, etc.), with or without the use of a vinyl compound such as methyl acrylate and 2-hydroxyethyl acrylate.

The adhesive composition of the present invention is outlined as follows. The first adhesive composition is characterized by comprising a photopolymerization initiator or curing agent and the compound represented by the formula [I]

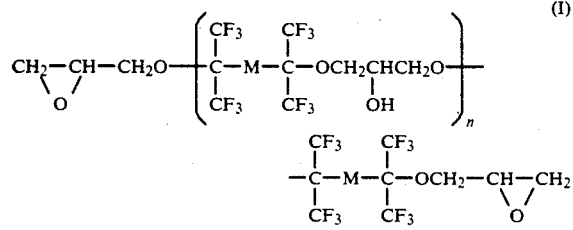

wherein M is as defined above, n is zero or a positive number.

The second adhesive composition is characterized by comprising a polymerization initiator and the compound represented by the formula [II]

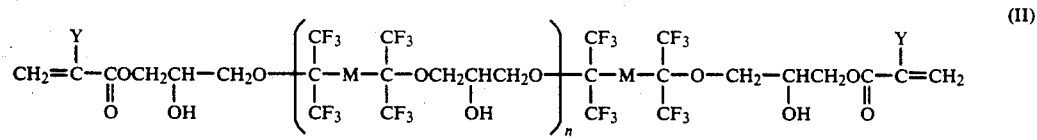

wherein M is as defined above, n is zero or a positive number, Y is H or CH₃.

The present adhesive composition may contain, as other components, for example, conventional epoxy resin, acrylate resins, such as epoxy (meth)acrylate resin, urethane acrylate and polybutadiene acrylate and modified products thereof, diluent, curing agent, initiator and coupling agent.

The amount of the fluorine-containing compound of the formula (I) or (II) in the adhesive composition is preferably at least 1% by weight in order to lower the refractive index and enhance water-resistance, heat-resistance and adhesive strength. With less than this amount, the effects are lowered.

Examples of epoxy compounds of the formula (I) of the present invention are compounds having the following structures:

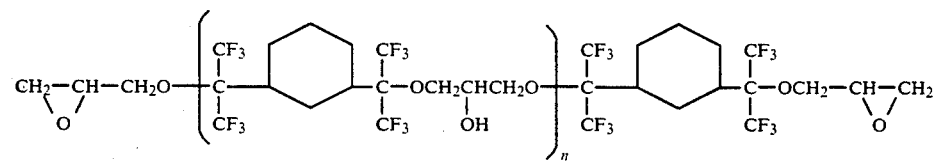

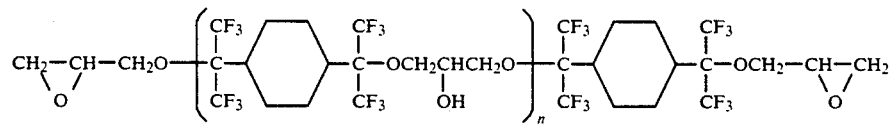

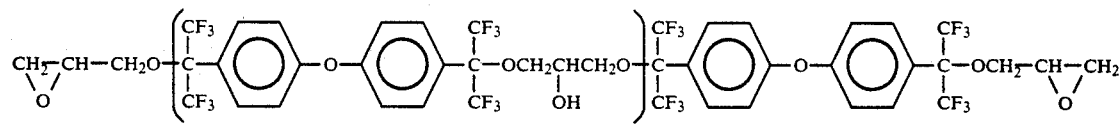

In the above, n is zero or a positive number.

Further, epoxy acrylate compounds of the formula (II) of the present invention include compounds having the following structures:

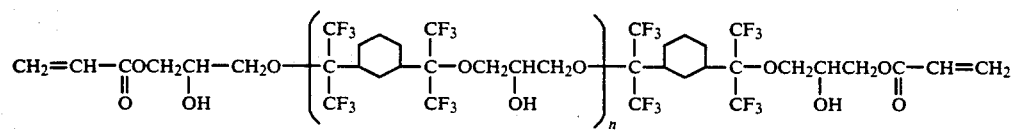

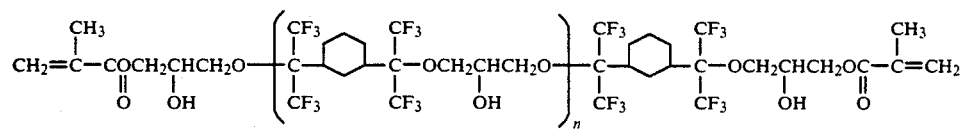

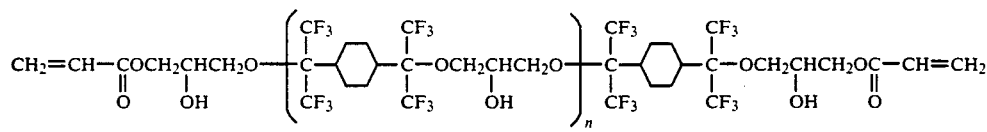

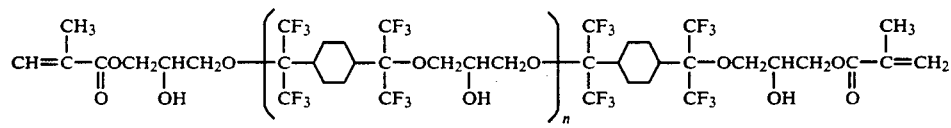

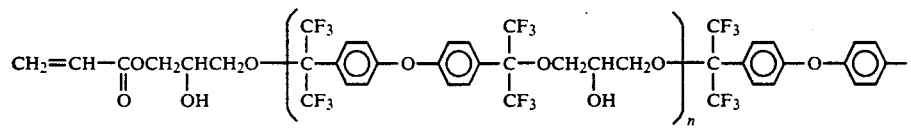

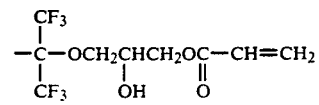

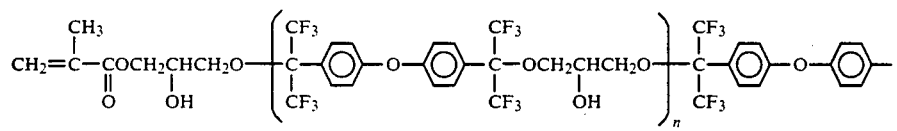

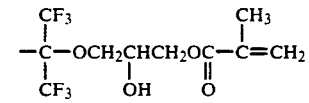

In the above, n is zero or a positive number.

With respect to the epoxy compound of the formula (I) and the epoxy acrylate compound of the formula (II), n is preferably 0 to 4 because the compound having a n-value larger than 4 is solid and is difficult to coat.

In the present adhesive composition, examples of epoxy resins conjointly used with the epoxy resin of the formula (I) are those having the following structure, novolak epoxy resin, o-cresol novolak epoxy resin and epoxied polybutadiene.

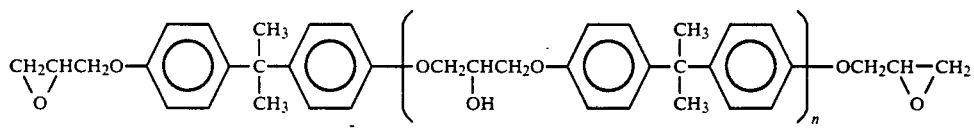

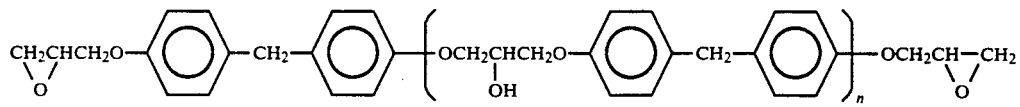

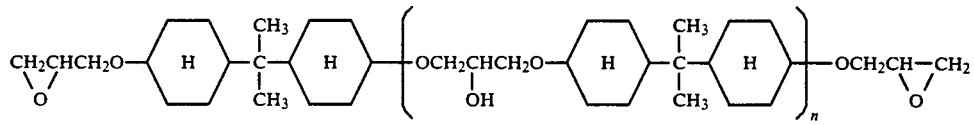

(n is zero or a positive number)

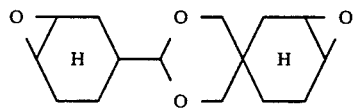

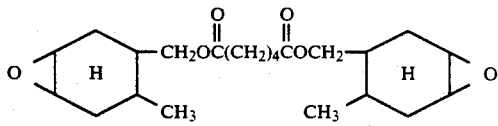

Examples of useful curing agents are polyamines, polyols and acid anhydrides, which are conventionally used for epoxy resins.

Polyamines include: diethylenetriamine (DETA), triethylenetetramine (TETA), tetraethylenepentamine (TEPA), dipropylenetriamine (DPTA), bis(hexamethylene)triamine, 1,3,6-trisaminomethylcyclohexane (TMAH), trimethylhexamethylenediamine (TMD), polyetherpolyamines, diethylaminopropylamine (DEAPA), methanediamine (MDA), isophoronediamine (IPD), bis(4-amino-3-methylcyclohexyl)methane, N-aminoethylpiperadine (AEP), m-xylylenediamine (MXDA), m-phenylenediamine (MPDA), diaminodiphenylmethane (DDM), diaminodiphenylsulfone (DDS), 3,9-bis(3-aminopropyl)-2,4,8,10-tetraspiro[5,5]undecane (ATU) and cyanoethylated polyamines.

In addition, polyamideamines can be used which are prepared mainly by condensation of dimer acid and polyamine. Examples of polyamideamines are: Tomide (trade name, same as hereinafter, Fuji Chemical Ind. Ltd.), Versamide (Henkel Hakusui Ltd.), Laquamide (Dainippon Ink and Chemicals, Inc.), Polyamide (Sanyl Chemical Industries, Ltd.), EPOMIK (Mitsu Petrochemical CO., Ltd.) and Sunmide (Sanwa Chemicals CO., Ltd.).

Examples of polyols are phenol novolak, o-cresol novolak, polyvinyl phenol, bromide thereof, 2,2-bis(4'-oxyphenyl)propane and 2,2-bis(4'-oxyphenyl)perfluoropropane.

Examples of acid anhydrides are anhydrides of each of: phthalic acid, trimellitic acid, pyromellitic acid and benzophenonetetracarboxylic acid; anhydride of each of maleic acid, succinic acid, tetrahydrophthalic acid and methyltetrahydrophthalic acid; anhydride of each of methylnadic acid, dodecenylsuccinic acid, hexahydrophthalic acid, methylhexahydrophthalic acid and methylcyclohexenetetracarboxylic acid; anhydride of each of chlorendic acid and tetrabromophthalic acid.

The catalyst for thermal curing includes: imidazoles, Lewis acids and the like, which are used for curing the conventional epoxy resins.

Examples of imidazoles are: 2-methylimidazole (2MZ), 2-ethyl-4-methylimidazole (2E4MZ), 2-undecylimidazole, 2-heptadecylimidazole, 2-phenylimidazole (2PZ), 1-benzyl-2-methylimidazole (1B2MZ), 1-cyanoethyl-2-methylimidazole (2MZCM), 1-dyanoethyl-2-ethyl-4-methylimidazole (2E4MZ.CN), 1-cyanoethyl-2-undecylimidazole, 1-cyanoethyl-2-undecylimidazolium. trimellitate, 1-cyanoethyl-2-phenylimidazolium. trimellitate (2PZ.CNS), 2-methylimidazolium. isocyanurate, 2-phenylimidazolium.isocyanurate, 2,4-diamino-6-[2-methylimidazolyl-(1)]-ethyl-s-triazine (2MZ-AZINE), 2,4-diamino-6-[2-ethyl-4-methylimidazolyl-(1)] -ethyl-s-triazine (2E4MZ-AZINE) and 2-phenyl-4,5-dihydroxymethylimidazole (2PHZ).

Lewis acids include: boron trifluoride ($BF_3$), zinc chloride ($ZnCl_2$), tin tetrachloride ($SnCl_4$), aluminum chloride ($AlCl_3$), phosphorus pentafluoride ($PF_5$), arsenic pentafluoride ($AsF_5$) and antimony pentafluoride ($SbF_5$), and are used usually in the form of an amine-complex.

As a curing catalyst in photopolymerization are used: diazonium salts, sulfonium salts, iodonium salts, selenium salts and like compounds, which are known to be effective for epoxy resins.

The diazonium salt is represented by the formula A:

$$Ar-N_2^+X^- \quad (A)$$

Ar includes for example o-, m- or p- nitrophenyl, methoxyphenyl, 2,5-dichlorophenyl, p-(N-morpholino)-phenyl and 2,5-diethoxy-4-(p-trimercapto)phenyl. $X^-$ is an anion and includes $BF_4^-$, $FeCl_4^-$, $PF_6^-$, $AsF_6^-$ and $SbF_6^-$.

As a sulfonium salt, these are used: bis[4-(diphenylsulfonio)phenyl]sulfide-bis-hexafluorophosphate and bis[4-(diphenylsulfonio)phenyl]sulfide-bis-hexafluoroantimonate, and compounds disclosed on page 15, line 24 to page 18, line 1 of Japanese examined patent publication No. 42688/1984.

As a iodonium salt these are used: di(4-tert-butylphenyl)iodoniumhexafluorophosphate and di(4-tert-butylphenyl)iodoniumhexafluoroantimonate, and compounds disclosed on page 11, line 28 to page 12, line 30 of Japanese examined patent publication No. 42688/1984.

Selenium salts include: triphenylseleniumhexafluoroantimonate, 4-tert-butylphenyldiphenyltetrafluoroborate and 2,3-dimethylphenyldiphenylhexafluoroantimonate.

Examples of diluting agents are: butyl glycidyl ether, 2-ethylhexyl glycidyl ether and like alkyl ($C_{2\sim 25}$) monoglycidyl ether, butanediol diglycidyl ether, 1,6-hexanediol diglycidyl ether, neopentyl glycol diglycidyl ether, dodecanediol diglycidyl ether, pentaerythritol polyglycidyl ether, trimethylolpropane polyglycidyl ether, glycerol polyglycidyl ether, phenyl glycidyl ether, resorcin diglycidyl ether, p-tert-butylphenyl glycidyl ether, allyl glycidyl ether, tetrafluoropropyl glycidyl ether, octafluoropentyl glycidyl ether, dodecafluorooctyl diglycidyl ether, styrene oxide, limonene monoxide, α-pinene epoxide, β-pinene epoxide, cyclohexene epoxide, cyclooctene epoxide, vinylcyclohexene dioxide and the compounds of the following formulae

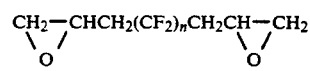

n = 1~20

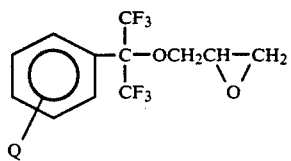

(Q is H, Cl, Br, $C_{1\sim 18}$ alkyl or $C_{1\sim 18}$ fluoroalkyl)

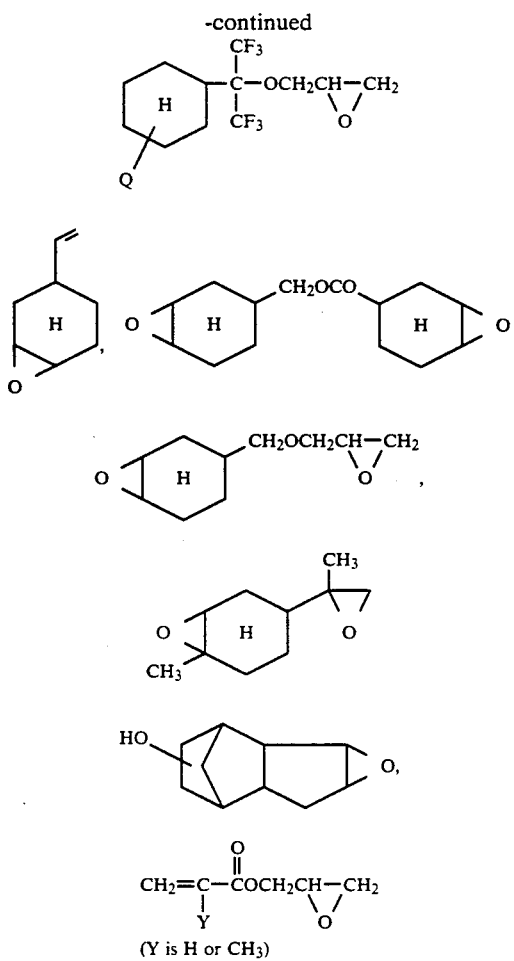

(Y is H or CH₃)

As a coupling agent (epoxy type) is used: carbon functional silane coupling agents such as γ-mercaptopropyltrimethoxysilane, γ-glycidoxypropyltrimethoxysilane and β-(3,4-epoxycyclohexyl)ethyltrimethoxysilane.

In the present adhesive composition, the epoxy (meth)acrylate compound of the formula (II) can be mixed with a known reactive oligomer or prepolymer having at least one carbon-carbon double bond in the molecule. Examples thereof are shown below.

(1) Ethylenically unsaturated polyesters obtained by condensation oligomerization of a polybasic carboxylic acid, polyol and ethylenically unsaturated monocarboxylic acid (2) Esters prepared by the reaction of a polyepoxy compound and ethylenically unsaturated monocarboxylic acid (3) Esters prepared by the reaction of a polyether-polyol and ethylenically unsaturated monocarboxylic acid (4) Ethylenically unsaturated polyurethanes prepared by reacting a polyisocyanate compound and hydroxyalkyl ester of an ethylenically unsaturated monocarboxylic acid Diallyl phthalate prepolymer, diallyl isophthalate prepolymer and diallyl terephthalate prepolymer can also be used.

More specific example of the polyester (1) is an oligoester (meth)acrylate obtained by condensation oligomerization of maleic anhydride, propylene glycol and (meth)acrylic acid.

More specific examples of the adducts (2) are an epoxy (meth)acrylate obtained from a bisphenol A diglycidyl ether and (meth)acrylic acid, and an epoxy (meth)acrylate obtained from a hydrogenated bisphenol A epoxide and (meth)acrylic acid.

More specific examples of the esters (3) are a polyethylene glycol di(meth)acrylate and polytetraethylene glycol di(meth)acrylate.

More specific example of the polyurethane (4) is a urethane (meth)acrylate, which is obtained by reacting an ethylene glycol and excess of diisocyanate compound to form a urethane prepolymer having isocyanate groups in both terminals and then by reacting therewith 2-hydroxyethyl (meth)acrylate.

Examples of initiators for curing are (a) a thermal polymerization initiation and (b) photopolymerization initiator.

The thermal polymerization initiator includes 2,2'-azobisisobutyronitrile, 2,2'-azobis(2,4-dimethylvaleronitrile), (1-phenylethyl)azodiphenylmethane, 2,3'-azobis(4-methoxy-2,4-dimethylvaleronitrile), dimethyl-2,2'-azobisisobutyrate, 2,2'-azobis(2-methylbutyronitrile), 1,1-azobis(1-cyclohexanecarbonitrile), 2-(carbamoylazo)-isobutyronitrile, 2,2'-azobis(2,4,4-trimethylpentane), 2-phenylazo-2,4-dimethyl-4-methoxyvaleronitrile, 2,2'-azobis(2-methylpropane) and like azo compounds; benzoyl peroxide, p-chlorobenzoyl peroxide and like diacyl peroxides; methyl ethyl ketone peroxide, cyclohexanone peroxide and like ketone peroxides; tert-butyl perbenzoate, tert-butyl peroxy-2-ethylhexoate and like peresters; tert-butyl hydroperoxide, cumene hydroperoxide and like hydroperoxides; di-tert-butyl peroxide, di-sec-butyl peroxide, dicumyl peroxide and like dialkyl peroxides; and aiaryl peroxides.

The photopolymerization initiators includes 2,2-diethoxyacetophenone, 2,2-dimethoxy-2-phenylacetophenone, benzophenone, methyl o-benzoylbenzoate, benzoin isobutyl ether, 2-chlorothioxanthone and 1-(4-isopropylphenyl)-2-hydroxy-2-methylpropane-1-one.

Examples of reactive diluents are: styrene, 1,6-hexanediol di(meth)acrylate, isobornyl (meth)acrylate, diallyl phthalate, diallyl isophthalate, diallyl terephthalate, butylene glycol dimethacrylate, 2-hydroxyethyl methacrylate, 2-hydroxypropyl methacrylate, lauryl acrylate, modified dicyclopentynyl acrylate, glycidyl methacrylate, tetrahydrofurfuryl acrylate, 1,3-butylene glycol dimethacrylate and the compounds of the following formulae having a caron-carbon double bond

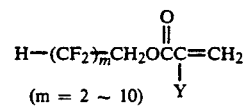

(m = 2 ~ 10)

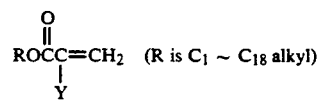

(R is C₁ ~ C₁₈ alkyl)

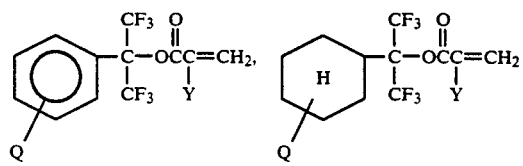

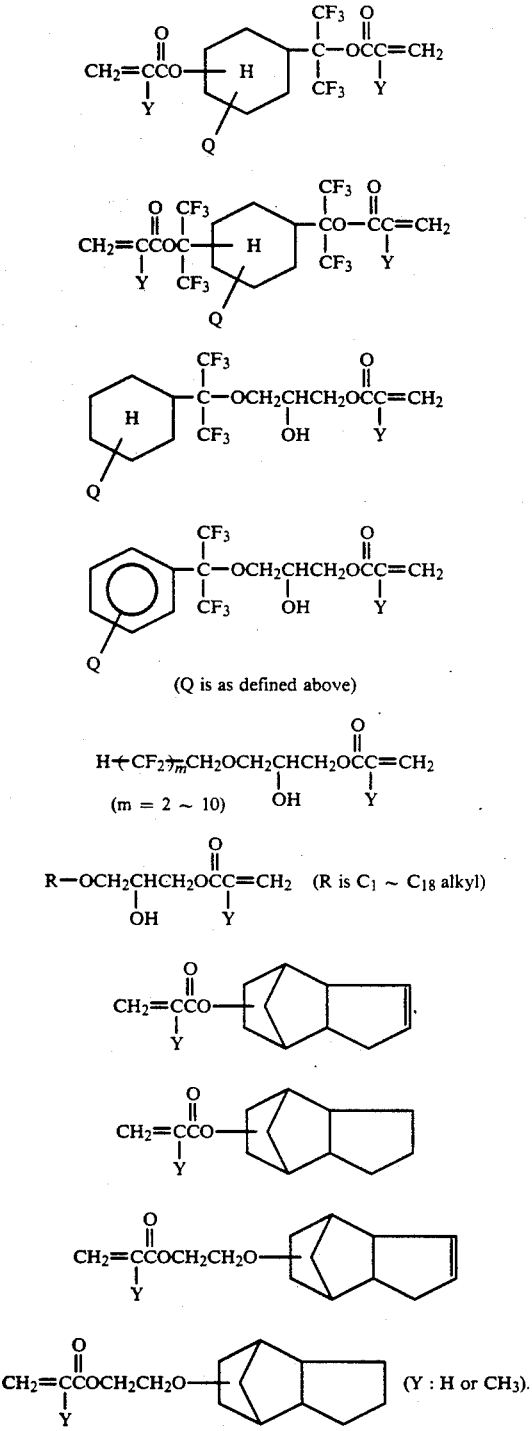

(Q is as defined above)

(m = 2 ~ 10)

(R is $C_1$ ~ $C_{18}$ alkyl)

(Y : H or $CH_3$).

Further, it is possible to add trimethoxysilylpropyl (meth)acrylate and like coupling agent to the present adhesive composition.

The fluorine-containing compounds of the present invention is excellent in heat-resistance, adhesive strength and water-resistance as well as has a low refractive index and match with an optical parts. The present compound can be cured by heat or irradiation of light, electron beams or like active energy rays in the presence of a curing agent, curing catalyst or initiator, and thus can provide an excellent adhesive. The cured product of the compound is useful as an optical material.

The present adhesive composition affords a cured product which has a low refractive index and can match with quartz and like optical parts in refractive index, and is excellent in water-resistance, heat-resistance and adhesive strength. Accordingly, the present adhesive composition is useful as an optical adhesive composition for optical parts used in photocommunication system.

The invention will be described in more detail below by showing Reference Examples, Examples and Comparison Examples.

FIG. 2-1 is a horizontal sectional view of the test piece for adhesion test made from BK 7 glass plate, FIG. 2-2 is a plane schematic view thereof.

FIG. 3-1 is a horizontal sectional view of the test piece for heat resistance test made from a glass plate, FIG. 3-2 is a plane schematic view thereof.

Figure 1:
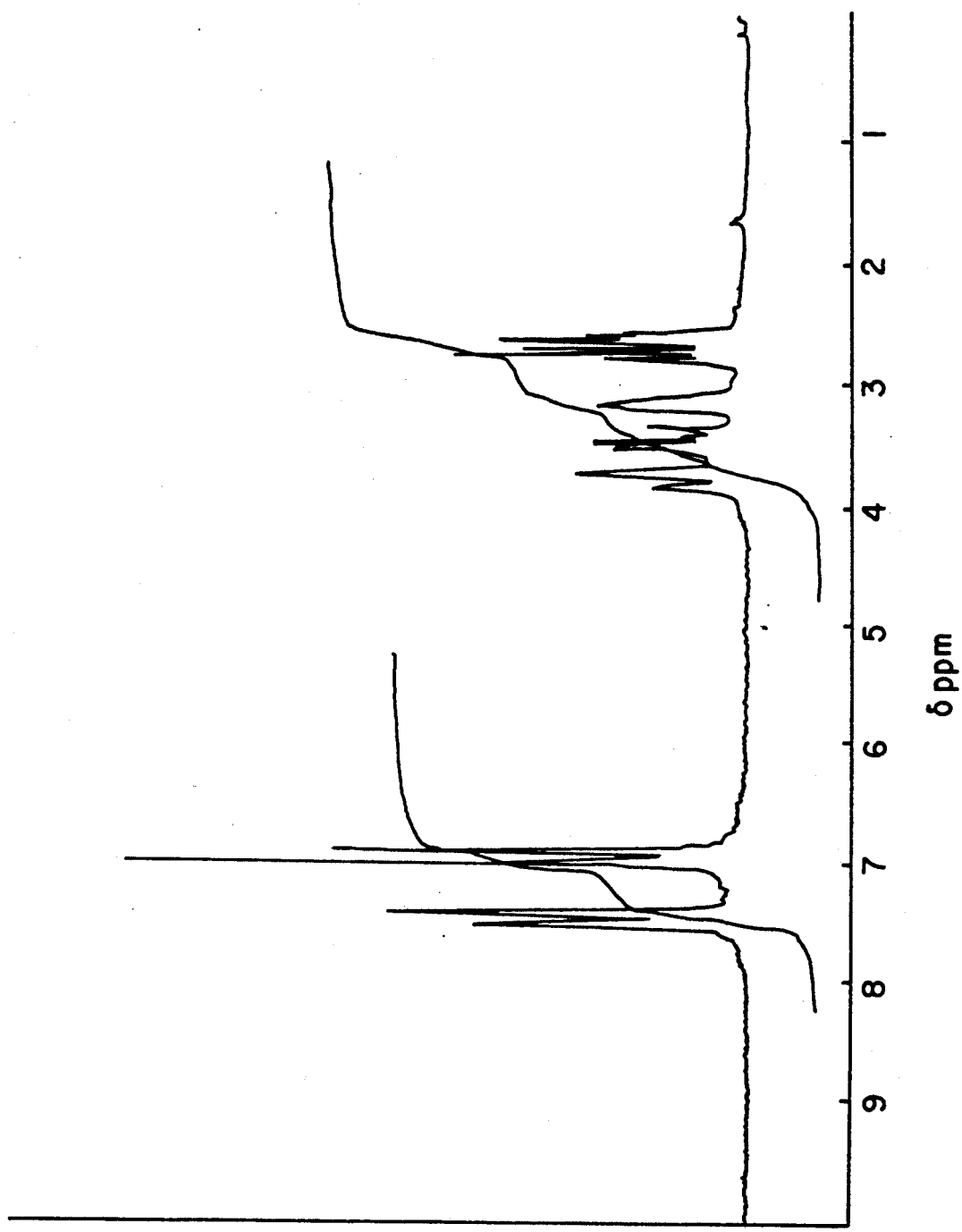
FIG. 1 is a $^1$H-NMR spectrum of the oil obtained in Example 5.

1:BK glass plate, 2,4,7: adhesive composition and adhesion portion, 3: slide glass, 5: optical fiber, 6: protective tube.

REFERENCE EXAMPLE 1

[Preparation of bis(1,1,1,3,3,3-hexafluoro-2-hydroxyisopropyl)benzene]

Into a one-liter flask equipped with a stirrer were placed 117 g (1.5 moles) of benzene and 31 g (0.23 mole) of anhydrous aluminum chloride and thereto was introduced 500 g (3 moles) of hexafluoroacetone in the rate of about 5 g/min. at temperature with stirring.

The reaction mixture was distilled at a reduced pressure to obtain 517 g (1.26 moles) of bis(1,1,1,3,3,3-hexafluoro-2-hydroxyisopropyl)benzene which is a mixture of m-isomer and p-isomer in 85:15 mole ratio and has a boiling point of 102° to 106° C./20 mmHg in a yield of 84% based on hexafluoroacetone.

REFERENCE EXAMPLE 2

Into a Hastelloy autoclave was placed a mixture of 300 ml of isopropanol and 300 g (0.73 mole) of bis(1,1,1,3,3,3-hexafluoro-2-hydroxyisopropyl)benzene which was prepared in Reference Example 1. To the mixture was added 30 g of rhodium supported by carbon powder (catalyst, rhodium content: 5% by weight based on the total weight). The mixture was heated at 155° C. with stirring, then pressurized at 60 kg/cm$^2$G with hydrogen and reacted for 4.5 hours.

The reaction mixture was cooled to room temperature and isopropanol was removed by distillation after separating the catalyst-supporting carbon powder. The residue was distilled at a reduced pressure to obtain 287 g (0.69 mole) of bis(1,1,1,3,3,3-hexafluoro-2-hydroxyisopropyl)cyclohexane which is fluorine-containing alicyclic diol and has a boiling point of 96° to 100° C./6 mmHG in a yield of 94%.

$^1$H-NMR (in $CCl_4$, δppm) 3.1(2H, s, OH), 1.1~2.5(10H, br, —CH—, —$CH_2$—).

EXAMPLE 1

To a mixture of 382 g (4.13 moles) of epichlorohydrin and 86 g (0.21 mole) of bis(1,1,1,3,3,3-hexafluoro-2-hydroxyisopropyl)cyclohexane (Compound A) obtained in Reference Example 2 were added 16.8 g (0.42 mole) of sodium hydroxide and 2 ml of water. The mixture was heated with stirring and reacted with reflux for 10 hours. The resulting sodium chloride was removed by filtration with use of a glass filter and the excess of epichlorohydrin was distilled off at a reduced pressure. The residue was checked by gel permeation chromatography (GPC) to find that the compounds of the formula (1) in which n was 0, 1 and 2 were contained in 93:6:1 (ratio of area on chromatogram). Conditions for GPC: column, Shodex, KF-801, KF-802, each 30 cm, solvent, chloroform. The reside was distilled to obtain 50 g of diglycidyl ether of the compound of the formula (1) wherein n was zero, namely Compound A. The ether had a boiling point of 138° to 150° C./1 mmHg.

$^1$H—NMR (in CCl$_3$, TMS standard, δppm)
1.4, 2.0 br 10H cyclohexane ring —CH—, —CH$_2$—

2.7 m 4H 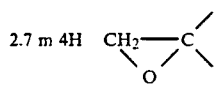

3.1 m 2H 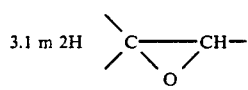

3.7 m 4H 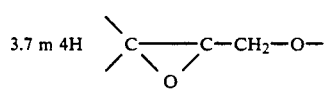

EXAMPLE 2

Compound A prepared in the same manner as in Reference Example 2 was allowed to place at 10° C. for a week to obtain precipitated crystals. The crystal was filtered and washed with trichlorotrifluoroethane to obtain 26 g (0.063 mole) of 1,4-bis(1,1,1,3,3,3-hexafluoro-2-hydroxyisopropyl)cyclohexane (Compound B). To a mixture of Compound B and 117 g (1.26 moles) of epichlorohydrin were added 5.1 g (0.13 mole) of sodium hydroxide and 0.6 ml of water and the mixture was refluxed for 10 hours with stirring. The resulting sodium chloride was removed by filtration and the excess of epichlorohydrin was distilled off. The residue was distilled to obtain 16 g of diglycidyl ether of Compound B having a boiling point of 147° to 151° C./1 mmHg.

$^1$H—NMR (in CCl$_3$, TMS standard, δppm)
1.4, 2.0 br 10H cyclohexane ring —CH—, —CH$_2$—

2.7 m 4H 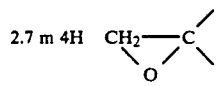

3.1 m 2H 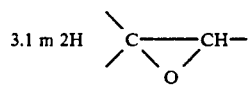

3.7 m 4H 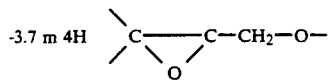

EXAMPLE 3

To 100 ml of toluene were added 18.0 g (0.25 mole) of acrylic acid and 57 g (0.108 mole) of diglycidyl ether of Compound A obtained in the same manner as in Example 1. Thereto were added 1 g of trimethylbenzylammonium chloride and 0.1 g of p-methoxyphenol and the mixture was heated to reflux with stirring. After 14 hours, the heating was stopped and the mixture was cooled to room temperature. The reaction mixture was washed with a saturated aqueous solution of sodium chloride until the aqueous layer does not indicate acidity and then dried over anhydrous sodium sulfate. Thereto was added 0.1 g of p-methoxyphenol and the mixture was heated at 80° to 90° C. at a pressure of 1 to 2 mmHg to remove a solvent and the compound of the formula (1) wherein n was zero and X was $$-CH_2CH-CH_2 \\ \phantom{-CH_2}| \phantom{CH-}| \\ \phantom{-CH_2}OH \phantom{C}\underset{\underset{O}{\parallel}}{O}CCH=CH_2$$

(Compound C) was obtained in a yield of 63 g as a viscous liquid.

IR (liquid film, cm$^{-1}$)

3400 OH,    2900 CH, CH$_2$,

1722 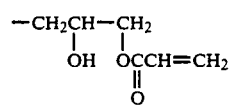 C=O,    1635 C=C,

1402 C=C

EXAMPLE 4

The compound of the formula (1) wherein n was zero and X was $$-CH_2CH-CH_2 \\ \phantom{-CH_2}| \phantom{CH-}| \\ \phantom{-CH_2}OH \phantom{C}\underset{\underset{O}{\parallel}}{O}C\underset{CH_3}{|}C=CH_2$$

(Compound D) was obtained in a yield of 64 g in the same manner as in Example 3 except that 21.5 g of methacrylic acid was used in place of acrylic acid.

IR (liquid film, cm$^{-1}$)

3400 OH,    2900 CH, CH$_2$,

1725 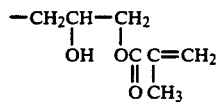 C=O,    1640 C=C,

-continued

1404 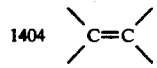

TEST EXAMPLE 1

Refractive index ($\eta_D^{23°C}$) was measured for the compounds of Examples 1 and 2 and the following Comparison Example 1. The results were given in Table 1.

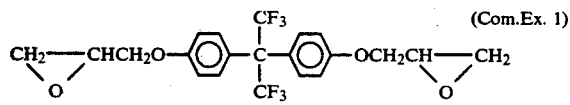 (Com.Ex. 1)

TABLE 1

| Compound | Ex. 1 | Ex. 2 | Com. Ex. 1 |
| --- | --- | --- | --- |
| Refractive index | 1.40 | 1.40 | 1.52 |

REFERENCE EXAMPLE 3

Into a four-necked flash equipped with a condenser cooled by dry-ice.methanol, stirrer and thermometer were placed 340 g (2 moles) of diphenyl ether and 8 g of anhydrous aluminum chloride and thereto was introduced hexafluoroacetone at 40° to 50° C. Hexafluoroacetone was continued to be introduced for 12 hours with addition of 16 g of anhydrous aluminum chloride every 3 hours, and was introduced in total amount of 664 g (4 moles). After completion of the reaction, the reaction mixture was diluted with isopropyl ether and washed with water until the aqueous layer does not indicate acidity. The organic layer was dried over anhydrous sodium sulfate and isopropyl ether was removed by distillation. The residue was distilled at a reduced pressure to obtain 753 g of the following compound (Compound E) having a boiling point of 144° to 146° C./0.6 to 0.7 mmHg.

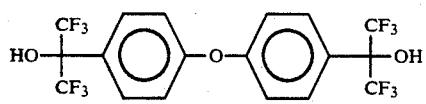

EXAMPLE 5

To a mixture of 2750 g of epichlorohydrin and 747 g of Compound E obtained in Reference Example 3 were added 120 g of sodium hydroxide and 5 ml of water. The mixture was mildly heated until reflux with stirring and then refluxed for 3 hours. Thereto was added 5 g of sodium hydroxide and the mixture was heated to reflux with stirring for further 10 hours. The resulting sodium chloride was removed by filtration with use of a glass filter (G-4) and the excess of epichlorohydrin was distilled off at a reduced pressure to obtain 910 g of a pale yellow oil as a residue. The residue was checked by GPC to find that the compounds of the formula (1) in which n was 0, 1 and 2 were contained in 89:8:3 (ratio of area on chromatogram). The compound wherein n was zero was diglycidyl ether of Compound E. FIG. 1 shows a $^1$H-NMR spectrum of the above oil.

EXAMPLE 6

In 300 ml of toluene was dissolved 57.6 g of acrylic acid and 184 g of diglycidyl ether of Compound E obtained in the same manner as in Example 5. Thereto were added 2.5 g of trimethylbenzylammonium chloride and 0.21 g of p-methoxyphenol and the mixture was heated at 90° C. with stirring for 13 hours. Further thereto were added 25 g of acrylic acid and 0.025 g of p-methoxyphenol and the mixture was maintained at 90° C. for 6 hours. After cooled to room temperature, 300 ml of isopropyl ether was added and the mixture was washed thrice with a saturated aqueous solution of sodium carbonate and then washed with a saturated aqueous solution of sodium chloride until the aqueous layer does not indicate basicity. The organic layer was dried over anhydrous sodium sulfate. Isopropyl ether and toluene were removed at a reduced pressure to obtain 198 g of the compound of the formula (1) wherein n was same as in Example 5 and X was $$-CH_2CH-CH_2$$
$$\phantom{-CH_2C}|\phantom{H-}|$$
$$\phantom{-CH_2C}OH\ OCCH=CH_2$$
$$\phantom{-CH_2CHOH\ O}\|$$
$$\phantom{-CH_2CHOH\ O}O$$

as a pale yellow viscous liquid (Compound F).

IR (liquid film, cm$^{-1}$)

| 3400 | OH, | 2900 | CH, CH$_2$, |
| --- | --- | --- | --- |
| 1720 | C=O, | 1635 | C=C, |

1404 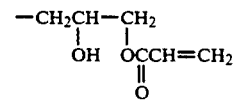

EXAMPLE 7

The compound of the formula (1) wherein n was same as in Example 5 and X was $$-CH_2CH-CH_2$$
$$\phantom{-CH_2C}|\phantom{H-}|$$
$$\phantom{-CH_2C}OH\ OC\ C=CH_2$$
$$\phantom{-CH_2CHOH\ }\|\ |$$
$$\phantom{-CH_2CHOH\ }O\ CH_3$$

(Compound G) was obtained in a yield of 203 g in the same manner as in Example 6 except that firstly 69 g of methacrylic acid and secondly 30 g of methacrylic acid were added in place of acrylic acid.

IR (liquid film, cm$^{-1}$)

| 3400 | OH, | 2900 | CH, CH$_2$, |
| --- | --- | --- | --- |
| 1720 | C=O, | 1640 | C=C, |

1402 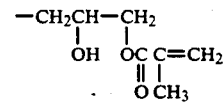

EXAMPLE 8

To the epoxy resin (CHEP) having the following formula, epoxy equivalent of 290 and refractive index of 1.405

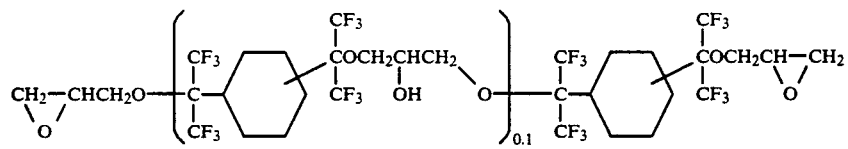

or the epoxy resin (DPEP) having the following formula, epoxy equivalent of 360 and refractive index of 1.47

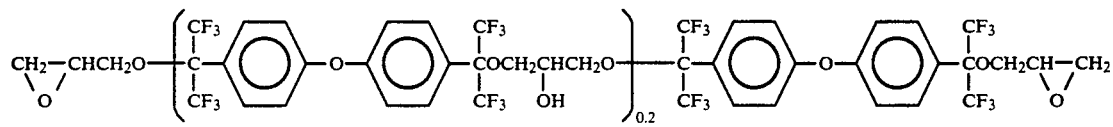

was added, as a curing agent, polyether polyamine (PEP A) which is a polyamine) type curing agent, boron trifluoride monoethylamine complex (BMA) which is a catalyst for thermal curing or $PF_6^-$ salt of triphenylsulfonium (TPS) which is a catalyst for photocuring to prepare adhesive compositions. The compositions were cured and checked for refractive index, adhesiveness, glass transition temperature (Tg) and resistance to hot water. The results were given in Table 2.

Figures 1, 2:
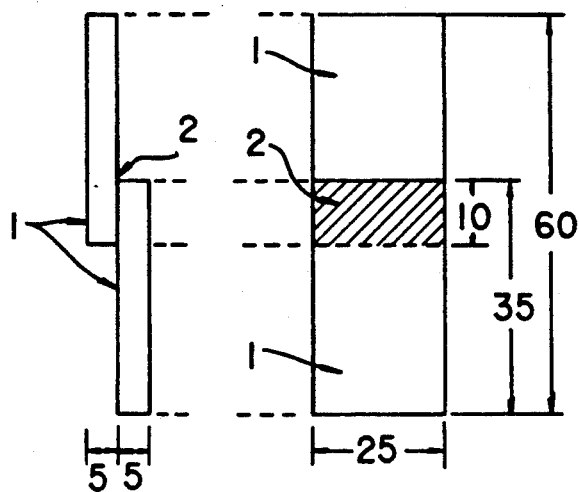

In the above, the refractive index ($\eta_D^{20}$) was measured by sodium D line at 589.3 μm at 20° C. with use of Abbé's refractometer. As the adhesiveness, shear adhesive strength was measured at 28° C. and at a tensile speed of 5 mm/min. with use of a BK 7 glass test piece shown in FIG. 2. Tg was measured by Differential Scanning Calorimetry (DSC). FIG. 2-1 is a horizontal sectional view of the test piece for adhesion test made from BK 7 glass plate. FIG. 2-2 is a plane schematic view thereof, and 1 is BK 7 glass plate, 2 adhesive composition and adhesion portion. The unit of numerals in Figures is mm.

Figures 1, 3:
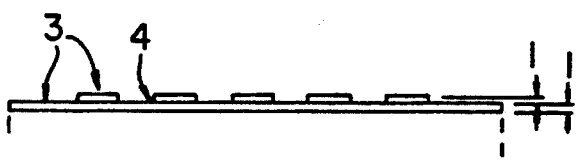
Figures 2, 3:
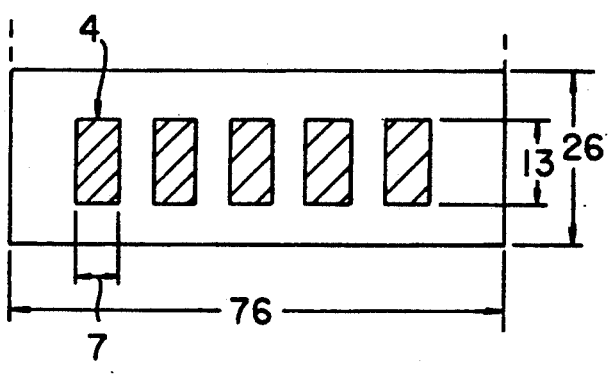

Heat resistance was checked by measuring a time for separation of a glass test piece shown in FIG. 3 after the immersion in hot water of 80° C. FIG. 3-1 is a horizontal sectional view of the test piece for heat resistance test made from a glass plate, FIG. 3-2 is a plane schematic view thereof, and 3 is a slide glass, 4 adhesive composition and adhesion portion. The unit of numerals in Figures is mm.

The adhesive composition was cured at 65° C. for 6 hours in case of using polyetherpolyamine as a curing agent, at 120° C. for 3 hours in case of boron trifluoride monoethylamine, and at 60° C. with irradiation of ultraviolet ray of 100 mJ/cm² by use of a ultra-high pressure mercury lamp in case of triphenylsulfonium salt.

The followings are an abbreviated name and structure of the diluting agents used.

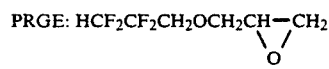

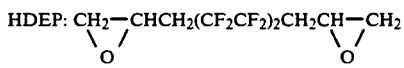

In the below are shown an abbreviated name and structure of the compounds used in Comparison Examples. AFEP

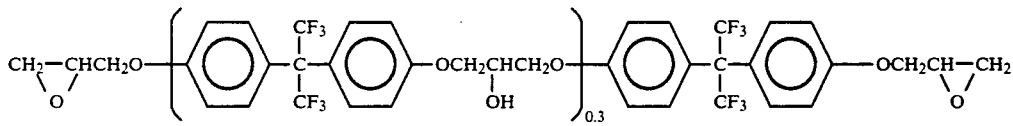

Epikote 828

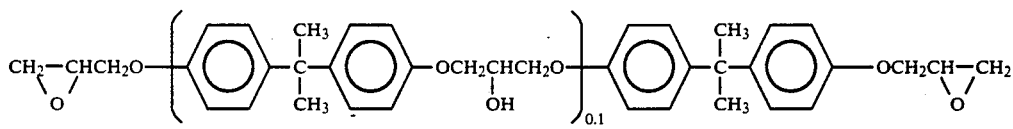

TABLE 2

| Epoxy resin | | Diluting agent | | Curing agent | |
|---|---|---|---|---|---|
| name | part | name | part | name | part |
| (a) CHEP | 100 | — | — | PEPA | 40 |
| (b) | 80 | PRGE | 20 | PEPA | 40 |
| (c) | 80 | HDEP | 20 | PEPA | 40 |
| (d) | 85 | PRGE | 15 | BMA | 5 |
| (e) | 70 | PRGE | 30 | TPS | 3 |
| (f) DPEP | 100 | — | — | PEPA | 40 |
| (g) | 80 | PRGE | 20 | PEPA | 40 |
| (h) | 80 | PRGE | 20 | BMA | 5 |
| (i) | 70 | PRGE | 30 | TPS | 3 |
| (j) CHEP/ AFEP | 53/27 | PRGE | 20 | PEPA | 40 |
| (k) | 40/40 | PRGE | 20 | PEPA | 40 |
| (l) | 27/53 | PRGE | 20 | PEPA | 40 |
| (m) | 53/27 | PRGE | 15 | BMA | 5 |
| (n) | 40/40 | PRGE | 15 | BMA | 5 |
| (o) | 27/53 | PRGE | 15 | BMA | 5 |
| Comparison | | | | | |

TABLE 2-continued

| | | | | | | |
|---|---|---|---|---|---|---|
| (p) | AFEP | 80 | BDDE | 20 | PEPA | 40 |
| (q) | Epikote 828 | 80 | BDDE | 20 | PEPA | 40 |

| | Refractive index | Adhesive strength (kgf/cm$^2$) | Tg (°C.) | Resistance to hot water (hr) |
|---|---|---|---|---|
| (a) | 1.442 | >190 | 53 | >72 |
| (b) | 1.444 | 110 | 84 | >72 |
| (c) | 1.494 | 100 | 45 | >72 |
| (d) | 1.417 | — | 42 | >24 |
| (e) | 1.431 | 156 | — | >24 |
| (f) | 1.505 | >150 | 68 | >72 |
| (g) | 1.503 | 128 | 52 | >72 |
| (h) | 1.485 | 140 | 59 | >72 |
| (i) | 1.494 | 147 | — | >24 |
| (j) | 1.484 | >110 | 53 | >72 |
| (k) | 1.472 | >100 | 46 | >72 |
| (l) | 1.459 | >140 | 40 | >72 |
| (m) | 1.475 | 140 | 81 | >24 |
| (n) | 1.462 | 157 | 82 | >24 |
| (o) | 1.449 | 128 | 22 | >24 |
| (p) | 1.518 | 102 | 76 | >72 |
| (q) | 1.564 | 110 | 70 | >24 |

In Table 2, CHEP and DPEP afford cured products having a lower refractive index than those of Comparison Examples. It is apparent in Examples compatibility in the refractive index with optical parts of low refractive index such as quartz glass ($\eta_D^{20} = 1.46$) is extremely improved. Further, it is clear that the present invention provides an adhesive composition which is sufficient in adhesive strength and excellent in resistance to hot water.

EXAMPLE 9

An adhesive composition containing an epoxy (meth)acrylate resin was cured by irradiation of ultraviolet ray of 100 mJ/cm$^2$. The cured product was checked in the same manner as in Example 8 in the refractive index, adhesive strength, Tg and resistance to hot water. Table 3 shows an abbreviated name and structure of the epoxy (meth)acrylate resin used.

TABLE 3

$$CH_2=CYCOOCH_2CHCH_2O\underset{OH}{-}(M'-OCH_2\underset{OH}{CH}CH_2O)_{\overline{n}}$$
$$-M'OCH_2\underset{OH}{CH}CH_2OCOCY=CH_2$$

| Name | Y | M' | n |
|---|---|---|---|
| CHEPA | H | 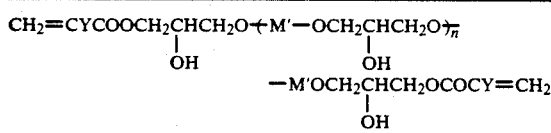 | 0.1 |
| CHEPMA | CH$_3$ | | |
| DPEPA | H |  | 0.2 |
| DPEPMA | CH$_3$ | | |
| AFEPA | H | 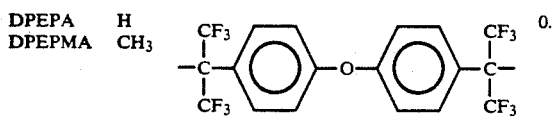 | 0.3 |

TABLE 3-continued $$CH_2=CYCOOCH_2CHCH_2O\underset{OH}{-}(M'-OCH_2\underset{OH}{CH}CH_2O)_{\overline{n}}$$
$$-M'OCH_2\underset{OH}{CH}CH_2OCOCY=CH_2$$

| Name | Y | M' | n |
|---|---|---|---|
| AEPA | H | 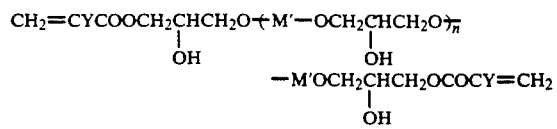 | 0.1 |

Shown below is an abbreviated name and structure of the diluting agent used.

As a photopolymerization initiator was used benzoin isobutyl ether (BBE). The results were given in Table 4.

TABLE 4

| Resin name | part | Diluting agent name | part | Photopolyn. initiator name | part |
|---|---|---|---|---|---|
| (a) CHEPA | 100 | — | — | — | — |
| (b) AHEPMA | 100 | — | — | — | — |
| (c) DPEPA | 100 | — | — | — | — |
| (d) DPEPMA | 100 | — | — | — | — |
| (e) DPEPMA | 80 | EGDMA | 20 | BBE | 3 |
| Comparison | | | | | |
| (f) AFEPA | 100 | — | — | — | — |
| (g) AEPA | 100 | — | — | — | — |

| | Refractive index | Adhesive strength (kgf/cm$^2$) | Tg (°C.) | Resistance to hot water (hr) |
|---|---|---|---|---|
| (a) | 1.428 | 93 | 50 | >24 |
| (b) | 1.431 | 85 | 48 | >24 |
| (c) | 1.492 | 115 | 64 | >24 |
| (d) | 1.495 | 89 | 62 | >24 |
| (e) | 1.500 | 79 | 65 | >24 |
| (f) | 1.528 | 45 | 93 | >24 |
| (g) | 1.565 | 60 | 92 | >24 |

From Table 4, cured products of Examples have lower refractive index than those of Comparison Examples and have an improved compatibility in the refractive index with optical parts of low refractive index. Further, the present composition is excellent in adhesive strength, resistance to hot water and Tg and is useful as an adhesive composition having a low refractive index.

EXAMPLE 10

Figure 4:
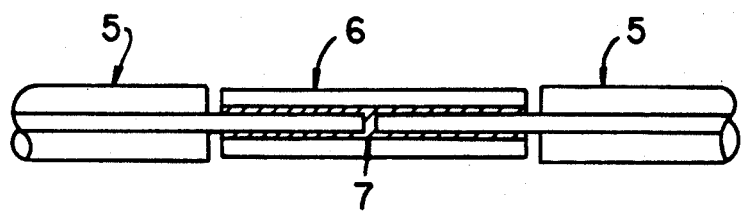
FIG. 4 is a schematic view of a test piece for reflection attenuation test.
Figure 5:
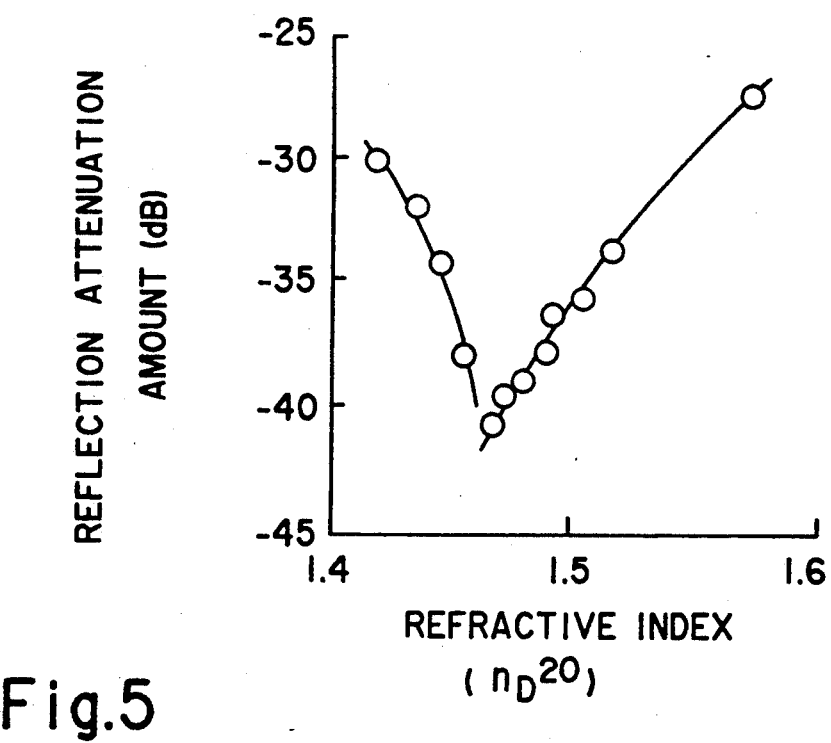
FIG. 5 is a graph showing a dependency of the reflection attenuation amount on the refractive index.

The amount of reflection attenuation of the present epoxy resin composition and epoxy (meth)acrylate resin composition was measured at a wavelength of 1.3 μm when used in the connecting part of an optical fiber shown in FIG. 4. The results are shown in FIG. 5. FIG. 4 is a schematic view of a test piece for reflection attenuation test, 5 is an optical fiber, 6 protective tube and 7 adhesive composition and adhesion portion. FIG. 5 is a graph showing a relation between the refractive index ($\eta_D^{20}$, abscissa) and the reflection attenuation amount (dB, ordinate). In the above, the refractive index was controlled by use of a mixture of at least two various compositions of Examples 1 and 2, and two kinds of resins of Comparison Examples.

With use of the present composition it is possible to achieve −35 dB or less in the reflection attention amount and is apparent that the compatibility in refractive index with a quartz fiber is greatly improved.

We claim:

1. Fluorine-containing alicyclic compounds represented by the formula

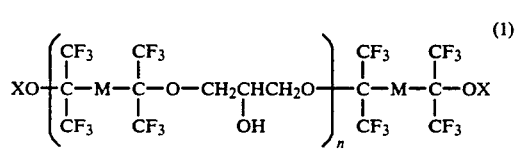

wherein M is a divalent organic group comprising at least one substituted or unsubstituted alicyclic hydrocarbon group, the alicyclic hydrocarbon group may be linked by O, S or CH$_2$, or may form a condensed ring and is selected from the following:

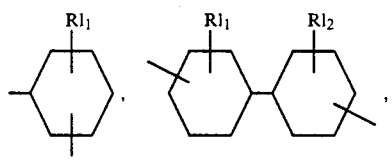

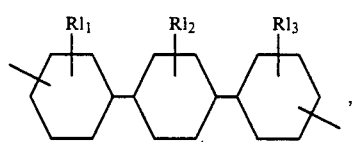

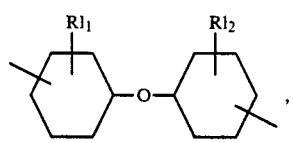

wherein R is a substituent, $l_1$, $l_2$ and $l_3$ are each zero or an integer of 1 to 10 and represent the number of the substituent R's, wherein said R's are same or different and are an alkyl group having 1 to 5 carbon atoms, OH, NH$_2$, halogen atom or a fluoroalkyl group having 1 to 20 carbon atoms, X is

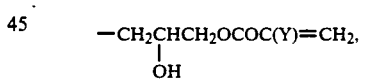

Y is H or CH$_3$,
n is zero to 30.

* * * * *